(12) United States Patent
Iwasaki et al.

(10) Patent No.: US 11,786,209 B2
(45) Date of Patent: Oct. 17, 2023

(54) ULTRASONIC DIAGNOSTIC APPARATUS AND IMAGE PROCESSING APPARATUS

(71) Applicant: Canon Medical Systems Corporation, Otawara (JP)

(72) Inventors: Ryosuke Iwasaki, Otawara (JP); Hiroki Takahashi, Tochigi (JP)

(73) Assignee: Canon Medical Systems Corporation, Otawara (JP)

( * ) Notice: Subject to any disclaimer, the term of this patent is extended or adjusted under 35 U.S.C. 154(b) by 105 days.

(21) Appl. No.: 17/015,689

(22) Filed: Sep. 9, 2020

(65) Prior Publication Data
US 2021/0085281 A1 Mar. 25, 2021

(30) Foreign Application Priority Data

Sep. 25, 2019 (JP) .................................. 2019-174050

(51) Int. Cl.
*A61B 8/06* (2006.01)
*A61B 8/08* (2006.01)
(Continued)

(52) U.S. Cl.
CPC .................. *A61B 8/06* (2013.01); *A61B 8/14* (2013.01); *A61B 8/488* (2013.01); *A61B 8/5276* (2013.01); *A61B 8/463* (2013.01)

(58) Field of Classification Search
None
See application file for complete search history.

(56) References Cited

U.S. PATENT DOCUMENTS

| 5,357,580 A | * | 10/1994 | Forestieri | ............ | G01S 15/8979 |
| | | | | | 382/128 |
| 5,609,155 A | * | 3/1997 | Guracar | .............. | G01S 7/52066 |
| | | | | | 600/453 |

(Continued)

FOREIGN PATENT DOCUMENTS

| JP | 4-269948 A | 9/1992 |
| JP | 11-276482 A | 10/1999 |

(Continued)

OTHER PUBLICATIONS

Japanese Office Action dated Feb. 28, 2023 in Japanese Patent Application No. 2019-174050, 3 pages.

*Primary Examiner* — Joel Lamprecht
*Assistant Examiner* — Ashish S Jasani
(74) *Attorney, Agent, or Firm* — Oblon, McClelland, Maier & Neustadt, L.L.P.

(57) ABSTRACT

According to one embodiment, an ultrasonic diagnostic apparatus includes an ultrasonic probe and processing circuitry. The processing circuitry receives a reflected wave signal of an ultrasonic wave via the ultrasonic probe. The processing circuitry generates a reception signal based on the received reflected wave signal. The processing circuitry calculates blood flow information based on the reception signal. The processing circuitry detects a magnitude of blood flow velocity change based on the blood flow information calculated at a plurality of points in time. The processing circuitry performs smoothing processing on the blood flow information in time direction at an intensity determined in accordance with the detected magnitude of blood flow velocity change.

15 Claims, 6 Drawing Sheets
(1 of 6 Drawing Sheet(s) Filed in Color)

(51) Int. Cl.
    *A61B 8/14*    (2006.01)
    *A61B 8/00*    (2006.01)

(56) References Cited

U.S. PATENT DOCUMENTS

| | | | | |
|---|---|---|---|---|
| 5,860,930 | A * | 1/1999 | Guracar | G01S 15/8979 |
| | | | | 600/455 |
| 5,899,864 | A * | 5/1999 | Arenson | G01S 7/52071 |
| | | | | 600/455 |
| 7,153,268 | B2 | 12/2006 | Li et al. | |
| 2003/0171668 | A1 | 9/2003 | Tsujino et al. | |
| 2007/0043294 | A1* | 2/2007 | Li | G01S 7/52026 |
| | | | | 600/455 |
| 2007/0060818 | A1* | 3/2007 | Iikubo | A61B 5/1075 |
| | | | | 600/437 |
| 2007/0083112 | A1* | 4/2007 | Dong | A61B 8/06 |
| | | | | 600/437 |
| 2007/0167770 | A1 | 7/2007 | Miyaki | |
| 2012/0101384 | A1 | 4/2012 | Migita | |
| 2015/0359507 | A1* | 12/2015 | Shibata | A61B 8/488 |
| | | | | 600/443 |
| 2019/0336107 | A1* | 11/2019 | Hope Simpson | A61B 8/488 |
| 2020/0214673 | A1* | 7/2020 | Yamamoto | A61B 8/56 |

FOREIGN PATENT DOCUMENTS

| | | |
|---|---|---|
| JP | 2002-224114 A | 8/2002 |
| JP | 2003-250804 A | 9/2003 |
| JP | 2006-14891 A | 1/2006 |
| JP | 2006-141994 A | 6/2006 |
| JP | 2007-504862 A | 3/2007 |
| JP | 2014-14518 A | 1/2014 |
| JP | 2014-198240 A | 10/2014 |
| WO | WO 2011/036891 A1 | 3/2011 |

* cited by examiner

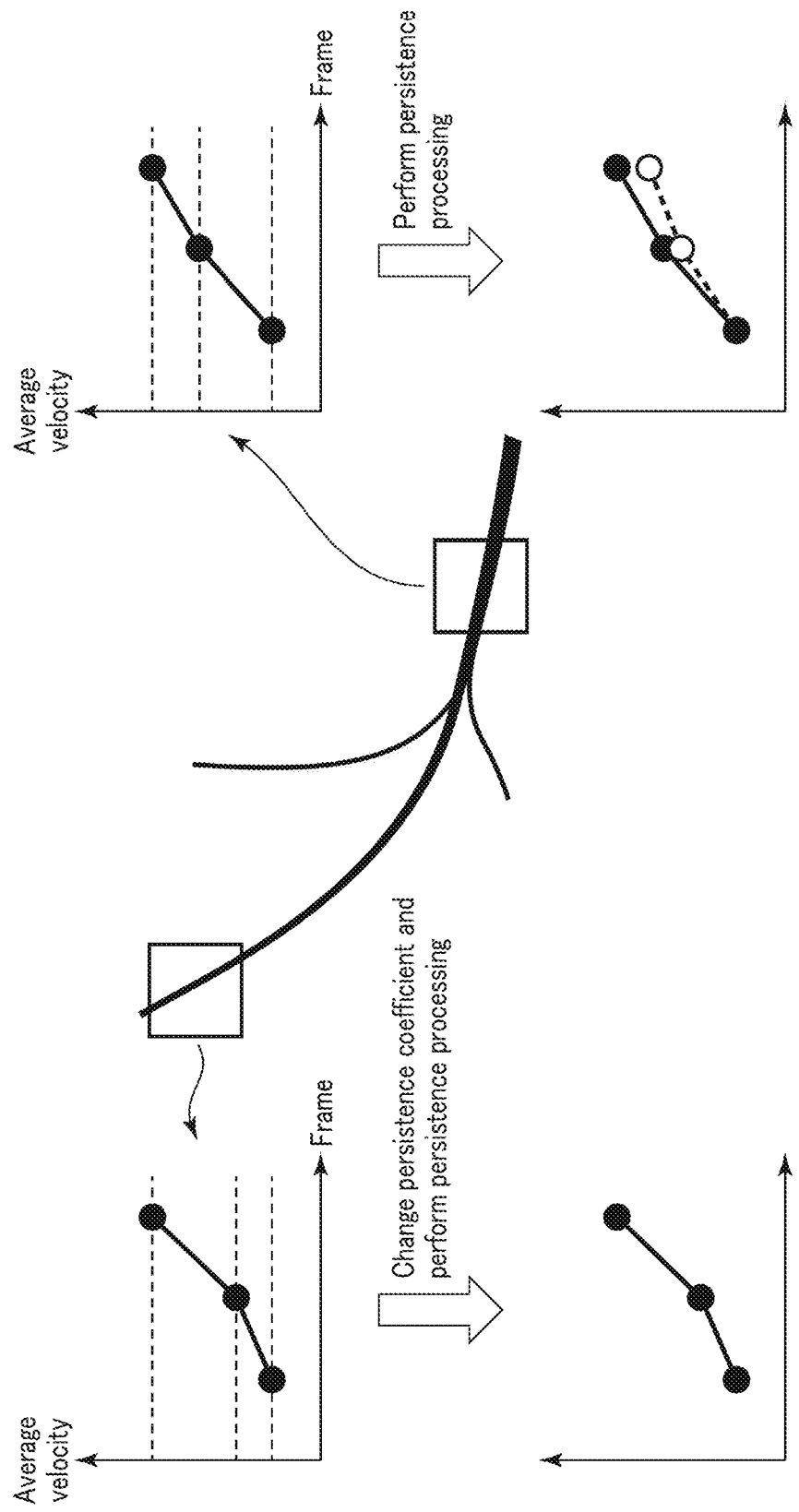
F I G. 4

ULTRASONIC DIAGNOSTIC APPARATUS AND IMAGE PROCESSING APPARATUS

CROSS-REFERENCE TO RELATED APPLICATIONS

This application is based upon and claims the benefit of priority from the prior Japanese Patent Application No. 2019-174050, filed Sep. 25, 2019, the entire contents of which are incorporated herein by reference.

FIELD

Embodiments described herein relate generally to an ultrasonic diagnostic apparatus and an image processing apparatus.

BACKGROUND

An ultrasonic diagnostic apparatus emits ultrasonic waves on a subject by an ultrasonic probe in which a plurality of ultrasonic transducers are aligned, and generates an ultrasonic image through receiving reflected ultrasonic waves with the ultrasonic probe.

The ultrasonic diagnostic apparatus can perform imaging blood flow in a subject body using a color flow mapping (CFM) method. Since the intensity of waves reflected from flowing blood is weaker than from tissue, the signal components belonging to tissue are suppressed by filtering in the measurement using the CFM method. If, however, a measurement target is peripheral blood vessels or a body part where blood flow is slow, etc., information relating to the blood flow may be undesirably suppressed by the filtering. To avoid this, smoothing processing is performed in a time-axis direction on the filtered signals so that a smooth image with reduced noise can be generated even in a case where a measurement target is peripheral blood vessels or a body part where blood flow is slow. This smoothing processing in the time-axis direction may be called "persistence processing", for example.

However, since an arithmetic mean or a weighted mean of received signals between frames is calculated in the persistence processing, structural sharpness in terms of space may be lost, or a sense of pulsation, which is fluctuations in terms of time, may be lost.

BRIEF DESCRIPTION OF THE DRAWINGS

The patent or application file contains at least one drawing executed in color. Copies of this patent or patent application publication with color drawing will be provided by the office upon request and payment of the necessary fee.

FIG. 4 is a diagram explaining time-direction smoothing processing shown in FIG. 2.

DETAILED DESCRIPTION

In general, according to one embodiment, an ultrasonic diagnostic apparatus includes an ultrasonic probe and processing circuitry. The processing circuitry receives a reflected wave signal of an ultrasonic wave via the ultrasonic probe. The processing circuitry generates a reception signal based on the received reflected wave signal. The processing circuitry calculates blood flow information based on the reception signal. The processing circuitry detects a magnitude of blood flow velocity change based on the blood flow information calculated at a plurality of points in time. The processing circuitry performs smoothing processing on the blood flow information in time direction at an intensity determined in accordance with the detected magnitude of blood flow velocity change.

Hereinafter, the ultrasonic diagnostic apparatus and image processing apparatus according to the present embodiment will be described with reference to the drawings. In the following embodiments, duplication of descriptions on portions provided with the same reference numbers will suitably be omitted, assuming that those portions perform the same operation. Hereinafter, a first embodiment will be described using drawings.

First Embodiment

Figure 1:
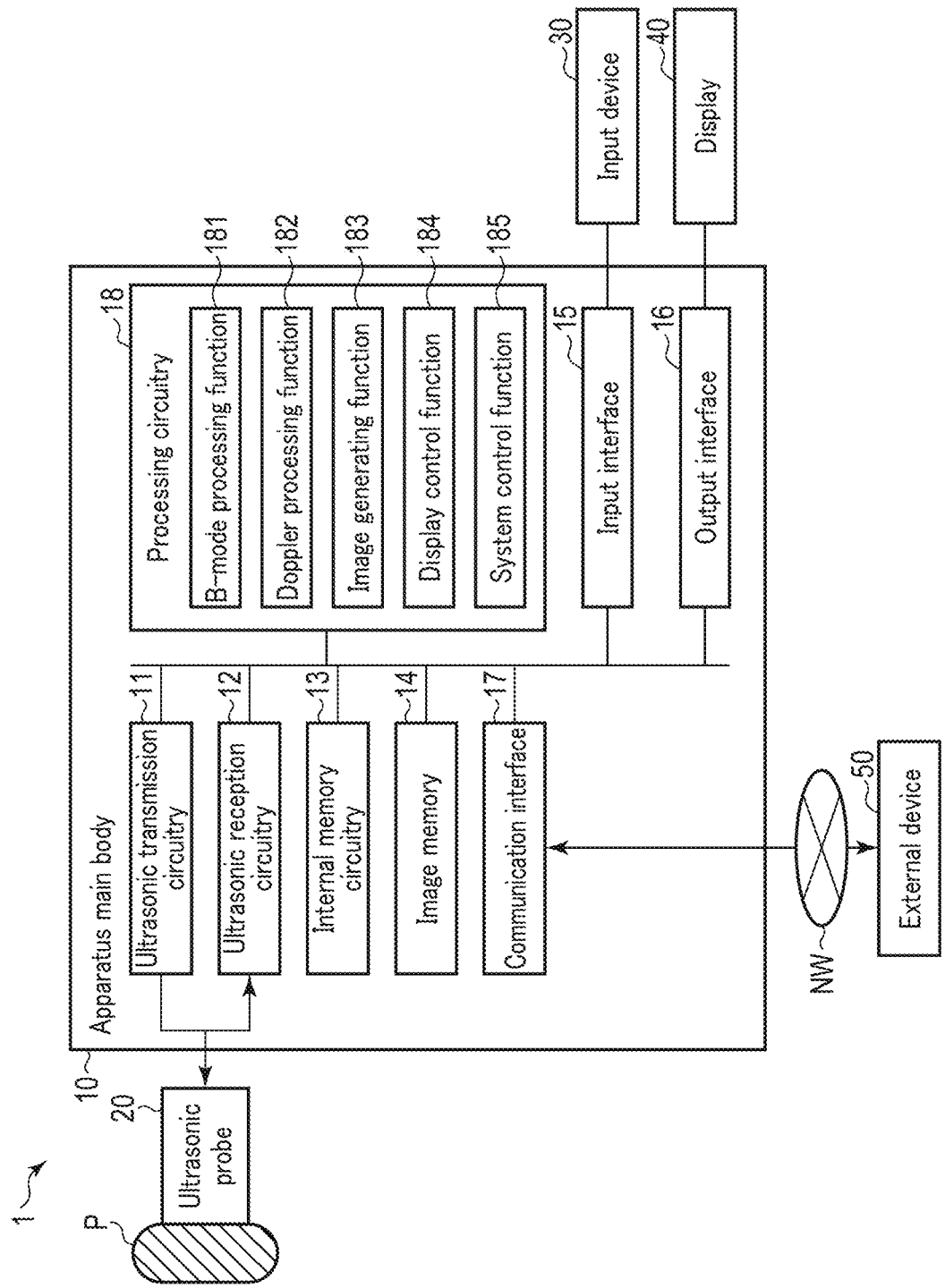
FIG. 1 is a block diagram showing a functional configuration of an ultrasonic diagnostic apparatus according to a first embodiment.

FIG. 1 is a block diagram showing an example of the functional configuration of an ultrasonic diagnostic apparatus 1 according to the first embodiment. The ultrasonic diagnostic apparatus 1 shown in FIG. 1 includes an apparatus main body 10 and an ultrasonic probe 20. The apparatus main body 10 is connected to the input device 30 and the display 40. The apparatus main body 10 is connected to an external device 50 via a network NW.

The ultrasonic probe 20 performs ultrasonic scanning on a scan area in a living body P, which is a subject, in accordance with a control of the apparatus main body 10. The ultrasonic probe 20 includes, for example, a plurality of piezoelectric transducers, a matching layer provided to the piezoelectric transducers, and a backing material that prevents propagation of ultrasonic waves from the piezoelectric transducers to the rear side. The ultrasonic probe 20 is detachably attached to the apparatus main body 10. The ultrasonic probe 20 may be provided with a button which is pressed when offset processing is performed or an ultrasonic image freezes.

The ultrasonic probe 20 is, for example, a one-dimensional linear array probe in which ultrasonic transducers are aligned in a predetermined direction, a two-dimensional array probe in which piezoelectric transducers are aligned in a matrix, or a mechanical four-dimensional probe capable of performing ultrasonic scanning while mechanically flapping a piezoelectric transducer line in directions orthogonal to the alignment direction.

The piezoelectric transducers generate ultrasonic waves based on a drive signal supplied from ultrasonic transmission circuitry 11 (which will be described later) included in the apparatus main body 10. Thus, ultrasonic waves are transmitted from the ultrasonic probe 20 to the living body P. When the ultrasonic probe 20 transmits ultrasonic waves to the living body P, the transmitted ultrasonic waves are sequentially reflected by a boundary showing discontinuity of acoustic impedance of living tissue in the living body P, and are received by the plurality of piezoelectric elements as reflected wave signals. The amplitudes of the received reflected wave signals depend on the difference in the acoustic impedance at the boundary showing discontinuity of the acoustic impedance that affects the reflection of ultrasonic waves. If the transmitted ultrasonic pulses are reflected in a bloodstream or on a surface of a cardiac wall, the frequencies of the reflected wave signals are shifted depending on velocity components in the direction of transmitting ultrasonic waves in a moving object due to the Doppler effect. The ultrasonic probe 20 receives the reflected wave signals from the living body P, and converts the reflected wave signals into electrical signals.

FIG. 1 merely illustrates a connection relationship between the ultrasonic probe 20 used for the ultrasonic scanning and the apparatus main body 10. However, a plurality of ultrasonic probes can be connected to the apparatus main body 10. The connected plurality of ultrasonic probes can be switched from one to another to discretionarily select which probe is to be used in the ultrasonic scanning.

The apparatus main body 10 is an apparatus that generates an ultrasonic image based on the reflected wave signals received by the ultrasonic probe 20. The apparatus main body 10 includes ultrasonic transmission circuitry 11, ultrasonic reception circuitry 12, internal memory circuitry 13, an image memory 14, an input interface 15, an output interface 16, a communication interface 17, and processing circuitry 18.

The ultrasonic transmission circuitry 11 is a processor that supplies a driving signal to the ultrasonic probe 20. The ultrasonic transmission circuitry 11 is implemented by, for example, a pulse generator, transmission delay circuitry, and pulser circuitry. The pulse generator repeatedly generates rate pulses for forming transmit ultrasonic waves at a predetermined pulse rate frequency (PRF). The transmission delay circuitry converges ultrasonic waves generated from the ultrasonic probe 20 as a beam, and applies, to each rate pulse generated by the pulse generator, a transmission delay time for each piezoelectric transducer required for determining a transmission directivity. The transmission direction or the transmission delay time that determines the transmission direction is stored in the internal memory circuitry 13, and is referred to when ultrasonic waves are transmitted. The pulser circuitry supplies driving signals (driving pulses) to the plurality of ultrasonic transducers provided in the ultrasonic probe 20 at a timing based on the rate pulse. By varying the delay time applied to each rate pulse by the transmission delay circuitry, the transmission direction from the piezoelectric transducer surface can be freely adjusted.

The ultrasonic transmission circuitry 11 has a function of changing a transmit frequency and a transmit drive voltage, etc. instantaneously based on an instruction from the processing circuitry 18 so as to perform a predetermined scan sequence. Particularly, the function of changing a transmit drive voltage is realized by a linear amplifier-type origination circuit capable of instantaneous switching of the voltage value, or a mechanism for electrically switching a power source unit to another.

The ultrasonic reception circuitry 12 is a processor that performs processing of various kinds on the reflected wave signals received by the ultrasonic probe 20 and generates a reception signal. The ultrasonic reception circuitry 12 is an example of a receiver. The ultrasonic reception circuitry 12 is realized by, for example, an amplifier, an A/D converter, a demodulator, and a beam former.

The preamplifier performs gain correction processing for each channel by amplifying reflected wave signals received by the ultrasonic probe 20. At this time, the preamplifier changes a gain value in accordance with a predefined time response, for example. The time response of the gain applied to the received signal in the amplifier is stored in the internal memory circuitry 13. The A/D converter converts the gain-corrected reflected wave signals into digital signals. The demodulator demodulates the digital signals to convert the digital signals into in-phase signals (I signals) and quadrature-phase signals (Q signals) of a baseband bandwidth. The beam former applies a delay time necessary for determining a reception directivity to the I signals and Q signals (hereinafter, "IQ signals"). The beam former sums a plurality of digital signals each provided with a delay time. By the beam former processing, a received signal with an enhanced reflected component is generated in a direction corresponding to the reception directivity.

The ultrasonic transmission circuitry 11 and the ultrasonic reception circuitry 12 share their components at least in part. When software beamforming is performed using the reflected wave signals, at least a part of the function of the above-described ultrasonic reception circuitry 12 (for example, the function relating to the received beamforming) may be performed by the processing circuitry 18 (which will be described later) on behalf of the ultrasonic reception circuitry 12. In other words, the processing circuitry 18 may serve as an example of a receiving unit.

The internal memory circuitry 13 includes, for example, a magnetic or optical storage medium, or a processor-readable storage medium such as a semiconductor memory. The internal memory circuitry 13 stores a control for realizing the ultrasonic transmission and reception. In addition, the internal memory circuitry 13 stores various data, such as diagnosis information, a diagnosis protocol, ultrasonic transmission conditions, ultrasonic reception conditions, signal processing conditions, image generation conditions, image processing conditions, a body mark generation program, display conditions, and a conversion table for presetting, for each diagnosis site, a range of color data for use in imaging. The above programs and data may be stored in the internal memory circuitry 13, for example. For example, the programs and data may be distributed as being stored in a non-volatile storage medium, and the programs and data may be read from the non-volatile storage medium and installed into the internal memory circuitry 13.

The internal memory circuitry 13 stores reception signals generated by the ultrasonic reception circuitry 12 and various ultrasonic image data generated by the processing circuitry 18, etc. in accordance with an operation that is input via the input interface 15. The internal memory circuitry 13 can transfer the stored data to the external device 50 via the communication interface 17.

The internal memory circuitry 13 may be a drive, etc. which reads and writes various types of information relative to a portable storage medium, such as a CD-ROM drive, a DVD drive, and a flash memory. The internal memory circuitry 13 can write the stored data into a portable storage medium, and store the data in the external device 50 via the portable storage medium.

The image memory 14 includes, for example, a magnetic storage medium, an optical storage medium, or a processor-readable storage medium such as a semiconductor memory. The image memory 14 stores image data corresponding to a plurality of frames immediately before a freeze operation input through the input interface 15. The image data stored in the image memory 14 is, for example, continuously displayed (cine-displayed).

The internal memory circuitry 13 and the image memory 14 are not necessarily implemented by separate storage devices. The internal memory circuitry 13 and the image memory 14 may be implemented by a single storage device. The internal memory circuitry 13 and the image memory 14 may be implemented respectively by a plurality of storage devices.

The input interface 15 receives various types of instructions from an operator through the input device 30. The input device 30 is, for example, a mouse, a keyboard, a panel switch, a slider switch, a trackball, a rotary encoder, an operation panel, or a touch command screen (TCS). The input interface 15 is connected to the processing circuitry 18 via, for example, a bus, converts an operation instruction that is input by the operator into an electrical signal, and outputs the electrical signal to the processing circuitry 18. The input interface 15 is not limited to being connected to physical operation components such as a mouse, a keyboard, etc. For example, the input interface may include circuitry which receives an electric signal corresponding to an operation instruction input from an external input device independently provided from the ultrasonic diagnostic apparatus 1, and outputs the electric signal to the processing circuitry 18.

The output interface 16 is an interface that outputs an electric signal from the processing circuitry 18 to the display 40. The display 40 is a display discretionarily selected from a liquid crystal display, an organic electro-luminescence (EL) display, a light-emitting diode (LED) display, a plasma display, a cathode ray tube (CRT) display, and the like. The output interface 16 is connected to the processing circuitry 18 via a bus for example, and outputs a signal supplied from the processing circuitry 18 to the display.

The communication interface 17 is connected to the external device 50 via the network NW for example, and performs data communication with the external device 50.

The processing circuitry 18 is a processor acting as a nerve center of the ultrasonic diagnostic apparatus 1, for example. The processing circuitry 18 executes a program stored in the internal memory circuitry 13 to realize a function corresponding to the program. The processing circuitry 18 has, for example, a B-mode processing function 181, a Doppler processing function 182, an image generation function 183, a display control function 184, and a system control function 185. In the present embodiment, the B-mode processing function 181, the Doppler processing function 182, the image generation function 183, the display control function 184, and the system control function 185 are realized by a single processor; however, the embodiment is not limited thereto. For example, processing circuitry may be constituted by combining a plurality of independent processors, and the respective processors may execute programs, thereby realizing the B-mode processing function 181, the Doppler processing function 182, the image generation function 183, the display control function 184, and the system control function 185. Dedicated hardware circuits capable of realizing the respective functions may also be incorporated.

The B-mode processing function 181 is a function of generating B-mode data, based on the reception signals received from the ultrasonic reception circuitry 12. Specifically, the processing circuitry 18 that enables the B-mode processing function 181 performs an envelope wave detecting process, a logarithmic compressing process, and the like on, for example, the reception signal received from the ultrasonic reception circuitry 12 to generate data (B-mode data) that expresses signal intensity by brightness. The generated B-mode data is stored in a raw data memory (not shown) as B-mode raw data on an ultrasound scan line (raster), which is two-dimensionally distributed.

The Doppler processing function 182 is a function of generating data (Doppler data) relating to blood flow information based on a Doppler effect of a moving object present in an imaging ROI (region of interest) set in a scanning area, by performing a frequency analysis on a reception signal received from the ultrasonic reception circuitry 12. The blood flow information includes an average velocity, a variance, and a power of blood flow in a subject, or a combination thereof. The generated Doppler data is stored in a raw data memory (not shown) as Doppler raw data on a two-dimensionally distributed ultrasound scan line.

The image generation function 183 is a function of generating various types of ultrasonic image data, based on data generated by the B-mode processing function 181 and/or the Doppler processing function 182. Specifically, the processing circuitry 18 that enables the image generation function 183 performs, for example, a RAW-pixel conversion to the B-mode raw data stored in the raw data memory, for example a coordinate conversion in accordance with a mode of ultrasonic scanning by the ultrasonic probe 20, so as to generate B-mode image data consisting of pixels.

The processing circuitry 18 performs, for example, a RAW-pixel conversion on the Doppler raw data stored in the raw data memory so as to generate Doppler image data in which blood flow information is visualized. The Doppler image data is average velocity image data, variance image data, power image data, or a combination thereof.

The display control function 184 is a function of causing the display 40 to display ultrasonic image data of various kinds generated by the image generation function 183, and is an example of a display control unit. Specifically, the processing circuitry 18 that enables the display control function 184, for example, controls the displaying of an image based on the B-mode image data, the Doppler image data, or image data included thereof generated by the image generation function 183, on the display 40.

The processing circuitry 18 that enables the display control function 184, for example, converts (scan-converts) a scan line signal sequence of ultrasound scanning into, for example, a scan line signal sequence in a video format used by for example television to generate ultrasound image data for display. The processing circuitry 18 may perform processing of various kinds, such as dynamic range, brightness, contrast, y curve corrections, and an RGB conversion, on the image data to be displayed. The processing circuitry 18 may add supplementary information, such as textual information of various parameters, a scale, or a body mark, to the image data to be displayed. The processing circuitry 18 may generate a user interface (GUI: Graphical User Interface) through which an operator inputs various instructions by the input interface 111, and causes the display 40 to display the GUI.

The system control function 185 is a function of controlling basic operations, such as the input and output and the ultrasonic transmission and reception relative to the ultrasonic diagnostic apparatus 1. The processing circuitry 18 that enables the system control function 185 receives, for example, an instruction to select from a variety of imaging modes through the input interface 15. The variety of imaging modes includes, for example, a B-mode and a blood flow imaging mode. The processing circuitry 18 controls the ultrasonic transmission circuitry 11 and the ultrasonic reception circuitry 12 so as to perform scanning with a selected imaging mode.

Next, the Doppler processing function 182 enabled by the processing circuitry 18 will be specifically described.

Figure 2:
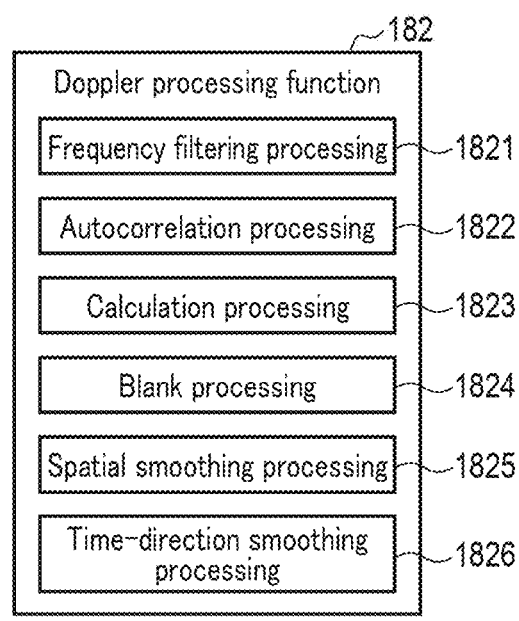
FIG. 2 is a diagram showing processing performed by a Doppler processing function shown in FIG. 1.

FIG. 2 is a diagram showing processing performed by the Doppler processing function 182 shown in FIG. 1. With the Doppler processing function 182 shown in FIG. 2, frequency filtering processing 1821, autocorrelation processing 1822, calculation processing 1823, blank processing 1824, spatial smoothing processing 1825, and time-direction smoothing processing 1826, are performed.

In the frequency filtering processing 1821, filtering based on a designated frequency characteristic is performed on a reception signal generated by the ultrasonic reception circuitry 12. A clutter signal included in the reception signal is removed by the frequency filtering processing 1821.

In the autocorrelation processing 1822, autocorrelation calculation is performed on the signal which has been subjected to the frequency filtering processing 1821. Specifically, for example, an autocorrelation value is calculated by calculating a complex conjugate of an IQ signal of a most-recent pulse from which a clutter signal has been removed and an IQ signal of an immediately previous pulse.

In the calculation processing 1823, blood flow information is calculated based on a received signal. The calculation processing 1823 is an example of a calculation unit. Specifically, for example, an average velocity and a variance are calculated from the autocorrelation value calculated in the autocorrelation processing 1822. Further, a power is calculated by adding a square of an absolute value of a real part of an IQ signal and a square of an absolute value of an imaginary part of the IQ signal.

In the blank processing 1824, one of the blood flow information items respectively calculated for samples is deleted based on a preset threshold. Specifically, if the average velocity calculated by the calculation processing 1823 is smaller than a predetermined velocity threshold, for example, the average velocity of this sample is deleted as being an average velocity originating from a clutter signal. If the variance calculated by the calculation processing 1823 is smaller than a predetermined variance threshold, the variance of this sample is deleted as being a variance originating from a clutter signal. If the power calculated by the calculation processing 1823 is smaller than a lower limit power threshold, or exceeds an upper limit power threshold, the power of this sample is deleted as being a power originating from a clutter signal.

In the spatial smoothing processing 1825, the data extracted by the blank processing 1824 is subjected to a smoothing filtering processing. Specifically, for example, a weighted mean is calculated for peripheral data of sample-of-interest data. A filter coefficient of a smoothing filter can be set as needed. For example, the smoothing filter may be a Gaussian filter. The order of performing the blank processing 1824 and the spatial smoothing processing 1825 may be inverted.

In the time-direction smoothing processing 1826, time-direction smoothing processing (persistence processing) is performed on the obtained data based on a magnitude of change in the blood flow velocity. The time-direction smoothing processing 1826 is an example of a time-direction smoothing processing unit. The persistence processing is a weighted calculation of data of a plurality of frames, for example. A persistence coefficient (frame weight) is set in accordance with a magnitude of change in the blood flow velocity. The persistence coefficient can also be called "intensity of time-direction smoothing processing". A persistence coefficient of 0 means the persistence processing is not performed.

Specifically, for example, the processing circuitry 18 that enables the time-direction smoothing processing 1826 obtains Doppler data of three points in time including a most-recent frame. In this case, these three points in time are at equal time intervals. The three points in time may be consecutive or non-consecutive frames. The processing circuitry 18 determines a coefficient of the persistence processing at a predetermined spatial point of a most-recent frame by detecting a magnitude of a velocity change at a spatial point corresponding to each of the three points in time.

The processing circuitry 18 sets a persistence coefficient to a first value if a velocity difference between the spatial points at the adjacent points in time among the three points in time, namely an acceleration rate, is increased. On the other hand, if the acceleration rate is not increased, the persistence coefficient is set to a second value. The second value is a value in which a weight on a point in time in the past is increased compared to the first value. The processing circuitry 18 performs a persistence processing on data of a most-recent frame with the set persistence coefficient. Doppler data is thereby generated.

Next, an example of measurement processing performed by the ultrasonic diagnostic apparatus 1 configured as described below is given.

Figure 3:
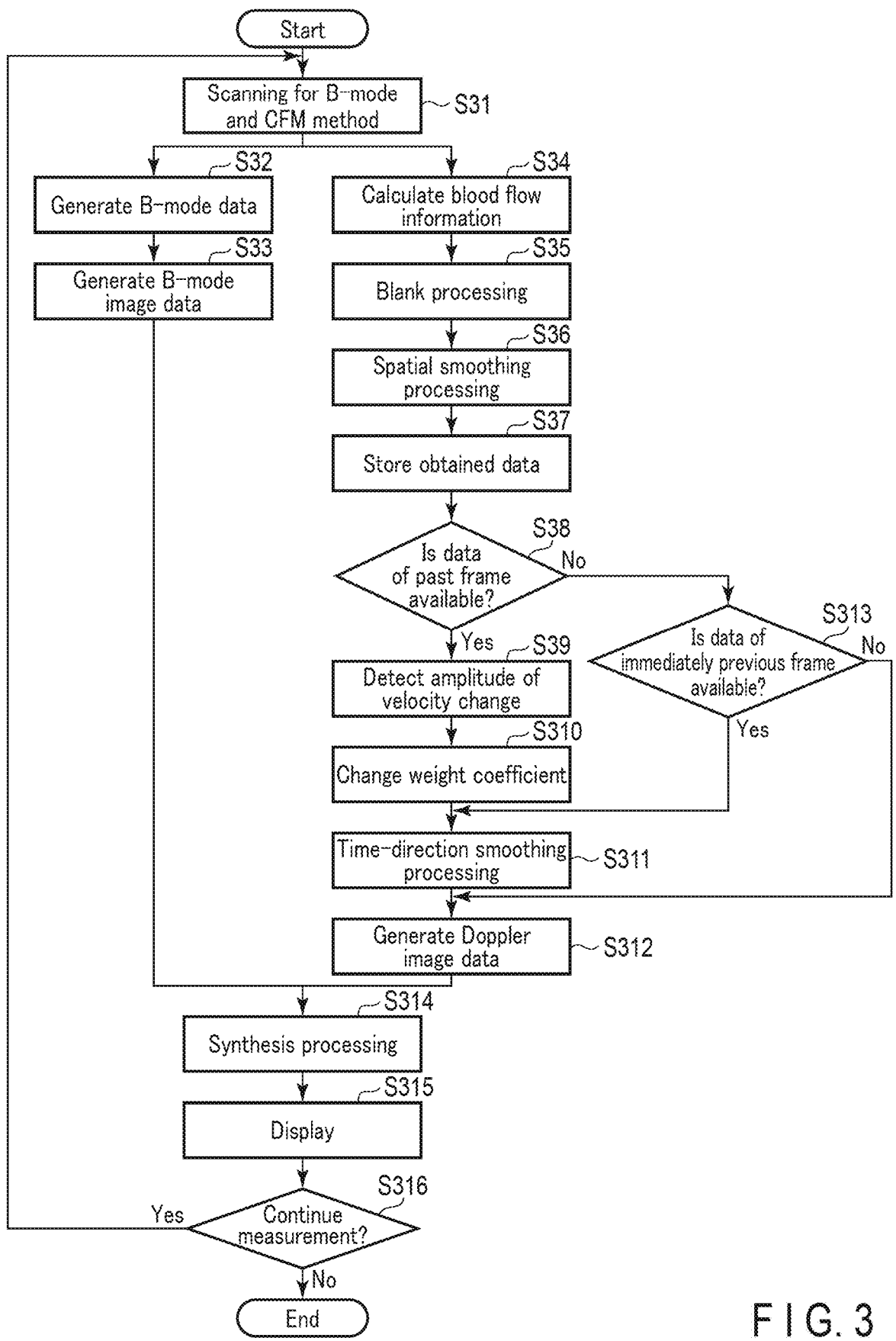
FIG. 3 is a flowchart of operations of processing circuitry when an ultrasound image is displayed on a display of the ultrasonic diagnostic apparatus shown in FIG. 1.

FIG. 3 is a flowchart 18 of operations of the processing circuitry 18 when an ultrasound image is displayed on the display 40 of the ultrasonic diagnostic apparatus 1 shown in FIG. 1. In the description of FIG. 3, an ROI for generating Doppler image data is set as a scan area via the input interface 15.

First, by an operator through the input interface 15, a blood flow imaging mode is selected and an instruction to start the selected blood flow imaging mode is input. Upon input of the instruction to start the blood flow imaging mode, the processing circuitry 18 performs the system control function 185. The processing circuitry 18 that enables the system control function 185 reads, for example, a scan sequence corresponding to the blood imaging mode from the internal memory circuitry 13. The processing circuitry 18 performs scanning based on the read scan sequence (step S31).

For example, the processing circuitry 18 reads ultrasonic transmission/reception conditions of the B-mode scanning from the internal memory circuitry 13 based on the scan sequence. The processing circuitry 18 sets the read ultrasonic transmission/reception conditions in the ultrasonic transmission circuitry 11. The ultrasonic transmission circuitry 11 transmits ultrasonic waves to the subject P from the ultrasonic probe 20 based on the set ultrasonic transmission/reception conditions.

Ultrasonic waves transmitted from the ultrasonic probe 20 to the subject P are sequentially reflected by the boundary showing discontinuity of the acoustic impedance of living tissue in the subject P, and are received as reflected wave signals by the ultrasonic probe 20. The ultrasonic reception circuitry 12 executes various types of processes on the reflected wave signals received by the ultrasonic probe 20 to generate a first reception signal. The generated first reception signal is maintained in a buffer (not shown), for example.

Subsequently, the processing circuitry 18 reads the ultrasonic transmission/reception conditions for the CFM method from the internal memory circuitry 13. The processing circuitry 18 sets the read ultrasonic transmission/reception conditions in the ultrasonic transmission circuitry 11. The ultrasonic transmission circuitry 11 transmits ultrasonic waves to the imaging ROI that has been set as a scan area, based on the set ultrasonic transmission/reception conditions.

The ultrasonic waves transmitted from the ultrasonic probe 20 to the subject P are sequentially reflected by the boundary showing discontinuity of the acoustic impedance of living tissue in the subject P, as the ultrasonic waves are receiving a frequency deviation originating from the velocity component of a moving object such as blood flow. The reflected signals are received by the ultrasonic probe 20 as reflected wave signals. The ultrasonic reception circuitry 12 executes various types of processes on the reflected wave signals received by the ultrasonic probe 20 to generate a second reception signal. The generated second reception signal is maintained in a buffer (not shown), for example.

When the B-mode scan is completed, the processing circuitry 18 that enables the B-mode processing function 181 generates B-mode data based on the first reception signal maintained in the buffer (step S32). Upon generation of the B-mode data, the processing circuitry 18 that enables the image generation function 183 generates B-mode image data based on the B-mode data (step S33).

Upon completion of a color Doppler scan, the processing circuitry 18 calculates blood flow information based on the second reception signal maintained in the buffer (step S34). Specifically, for example, the processing circuitry 18 performs the frequency filtering processing 1821, the autocorrelation processing 1822, and the calculation processing 1823 on the second reception signal to calculate an average velocity, a variance, a power of blood flow, or a combination of at least two of these.

Upon calculation of blood flow information, the processing circuitry 18 performs the blank processing (step S35). Specifically, for example, the processing circuitry 18 deletes blood flow information that does not satisfy the conditions based on a predetermined threshold from the blood flow information calculated for a plurality of sample data items.

Upon performance of the blank processing, the processing circuitry 18 performs spatial smoothing processing (step S36). Specifically, for example, the processing circuitry 18 calculates a value of blood flow information in each sample data by calculating a weighted mean based on the values of the blood flow information of the sample data and data of the periphery of the sample. The processing circuitry 18 causes the internal memory circuitry 13 to store the data obtained through the spatial smoothing processing (step S37).

Subsequently, the processing circuitry 18 performs the time-direction smoothing processing 1826.

In the time-direction smoothing processing 1826, the processing circuitry 18 determines whether or not the blood flow information obtained at a predetermined point in time in the past is stored in the internal memory circuitry 13 (step S38). Specifically, for example, the processing circuitry 18 determines whether or not the data obtained earlier than the most current frame by a predetermined number of frames, and the data obtained earlier than this data by the same number of frames are stored in the internal memory circuitry 13. The three points in time including the most current frame may be consecutive frames.

In the case where data of two points in time in the past is available (Yes in step S38), the processing circuitry 18 detects a magnitude of velocity change in data among the three points in time including the most recent frame for each piece of sample data (step S39). Specifically, for example, the processing circuitry 18 detects a sample in which a magnitude of velocity change (acceleration) increases as time elapses. The sample in which a magnitude of velocity change increases is a sample that satisfies the following requirement for example:

$$|V(z,x,t)|-2|V(z,x,t-1)|+|V(z,x,t-2)|>0 \quad (1)$$

In expression (1), (z,x) represents a spatial coordinate and t represents a frame number. Expression (1) an example in which the three points in time including the most current frame are consecutive frames.

The processing circuitry 18 changes the persistence coefficient used for the persistence processing for the sample in which a magnitude of velocity change increases as time elapses (step S310). The persistence processing is for example a weighted calculation expressed as follows:

$$V=(1-\alpha)V_{NEW}+\alpha V_{OLD} \quad (2)$$

In expression (2), $V_{NEW}$ and $V_{OLD}$ represent consecutive frames, for example. The processing circuitry 18 sets the persistence coefficient a in expression (2) to a first value, for example. On the other hand, for a sample in which the magnitude of the velocity change does not increase as time elapses, the persistence coefficient a is set to a second value which is closer to 1 than the first value is. If the first value is 0, the persistence processing is substantially not performed.

Upon setting of the persistence coefficient, the processing circuitry 18 performs the persistence processing for each sample using the set persistence coefficient (step S311). Doppler data is thereby generated. Upon generation of the Doppler data, the processing circuitry 18 that enables the image generation function 183 generates Doppler image data based on the Doppler image (step S312).

In step S38, if the blood flow information of two points in time in the past is not stored, the processing circuitry 18 determines whether or not the blood flow information of an immediately previous frame is stored (step S313). If the blood flow information of the immediately previous frame is stored (Yes in step S313), the processing circuitry 18 moves on to the processing in step S311. If the blood flow information of the immediately previous frame is not stored (No in step S313), the processing circuitry 18 treats the data after the spatial smoothing processing as Doppler data, and moves on to the processing in step S312.

FIG. 4 is a diagram explaining the time-direction smoothing processing 1826 shown in FIG. 2. The diagram shown at the center of FIG. 4 schematically shows the blood vessels. The blood vessels shown in FIG. 4 become more peripheral from the right side toward the top left. The graph shown on the right side of FIG. 4 shows sample data of the right-side area of the blood vessels, namely the area of relatively thick blood vessels. The graph shown on the left side of FIG. 4 shows sample data of the left-side area of the blood vessels, namely the area of peripheral blood vessels. The black dots in the graph represent the values of the blood flow information after being subjected to the spatial smoothing processing. The white dots in the graph represent the values of the blood flow information after being subjected to the time-direction smoothing processing. FIG. 4 adopts average velocity as the blood flow information.

In the sample data shown in the graph on the right side of FIG. 4, the magnitude of the acceleration does not increase as time elapses. In other words, the requirement of expression (1) is not satisfied. For this reason, for this sample data, the persistence coefficient is set to a second value, and weighted calculation as represented by expression (2) for example is performed.

In the sample data shown in the graph on the left side of FIG. 4, the magnitude of the acceleration increases as time elapses. In other words, the requirement of expression (1) is satisfied. For this reason, for this sample data, the persistence coefficient is set to a first value (herein 0), and weighted calculation as represented by expression (2) is performed for example.

Upon generation of the B-mode image data and the Doppler image data, the processing circuitry 18 that enables the image generation function 183 synthesizes the B-mode image data and the Doppler image data (step S314). Upon generation of the B-mode image data and the Doppler image data, the processing circuitry 18 enables the display control function 184 to display an image based on the generated ultrasonic image data on the display 40 (step S315). Subsequently, the processing circuitry 18 determines whether or not the measurement should be continued (step S316). For example, upon receipt of an instruction to cease the measurement from an operator via the input interface 15, or upon input of an operation to cease the measurement to the ultrasonic probe 20 (No in step S316), the processing circuitry 18 ceases the processing. If there is no input like the one described above (Yes in step S316), the processing circuitry 18 returns to step S31 and repeats the processing therefrom.

Figure 5:
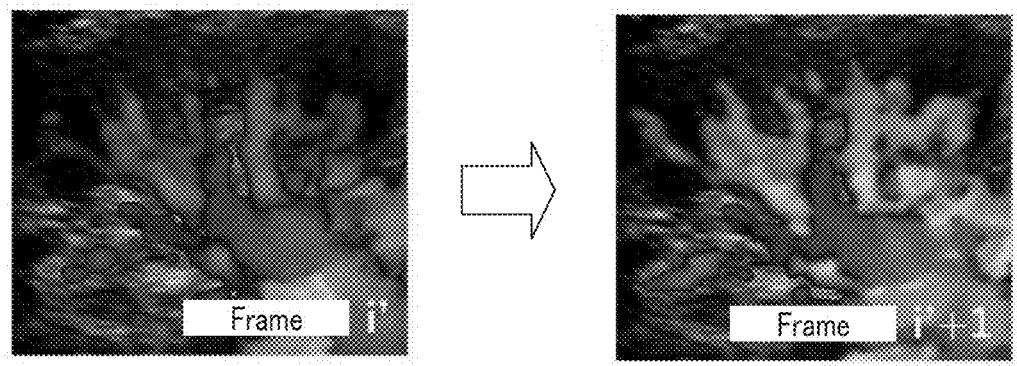
FIG. 5 is a diagram showing an ultrasound image of peripheral blood vessels generated through performance of the time-direction smoothing processing shown in FIG. 2.
Figure 6:
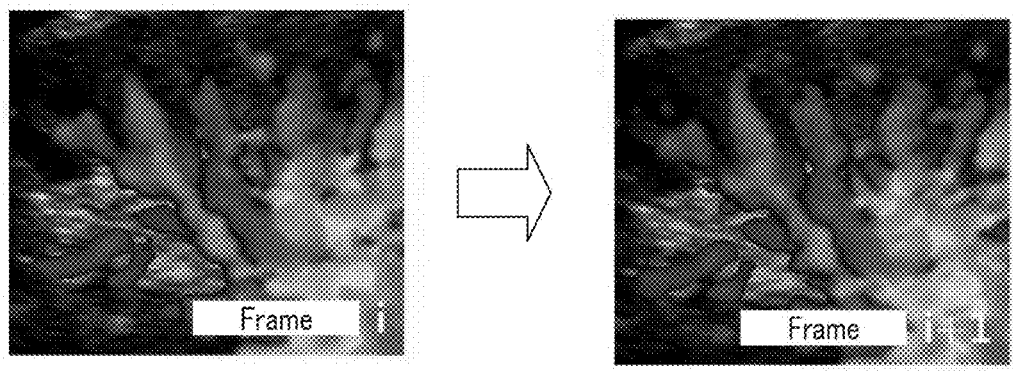
FIG. 6 is a diagram showing an ultrasound image of peripheral blood vessels generated through performance of conventional time-direction smoothing processing.

FIG. 5 is a diagram showing an example of an ultrasound image of peripheral blood vessels generated through performance of the time-direction smoothing processing 1826 shown in FIG. 2. FIG. 6 is a diagram showing an example of an ultrasound image of peripheral blood vessels generated through performance of conventional time-direction smoothing processing. FIGS. 5 and 6 show ultrasound images of two consecutive frames. In the example shown in FIG. 5, the persistence coefficient is changed in a direction in which the effect of the weighted calculation is attenuated; for this reason, the expression of how the blood flow ejects into the periphery is maintained, and the sharpness and a sense of pulsation of the blood flow image are maintained. In contrast, in the example shown in FIG. 6, the processing is performed with the preset persistence coefficient, and for this reason, the sharpness and a sense of pulsation are lost in the blood flow image.

Thus, in the present embodiment, the ultrasonic diagnostic apparatus 1 detects a magnitude of blood velocity change based on blood flow information calculated based on a reception signal, through the time-direction smoothing processing 1826 of the Doppler processing function 182. Furthermore, the ultrasonic diagnostic apparatus 1 is configured to perform the time-direction smoothing processing on the blood flow information using a persistence coefficient in accordance with a magnitude of change in detected blood flow velocity. It is thereby possible to, for an area in which there is a magnitude of change in blood flow velocity, apply a weight to information of a most-recent frame or display information of a most-recent frame only, and to maintain sharpness and a sense of pulsation in a blood flow image.

Other Embodiments

In the first embodiment, an example in which the time-direction smoothing processing 1826 is performed in the ultrasonic diagnostic apparatus 1 was given. However, the time-direction smoothing processing 1826 is performed not only in the ultrasonic diagnostic apparatus 1. Time-direction smoothing processing may be performed in an image processing apparatus 2 connected to the ultrasonic diagnostic apparatus 1.

Figure 7:
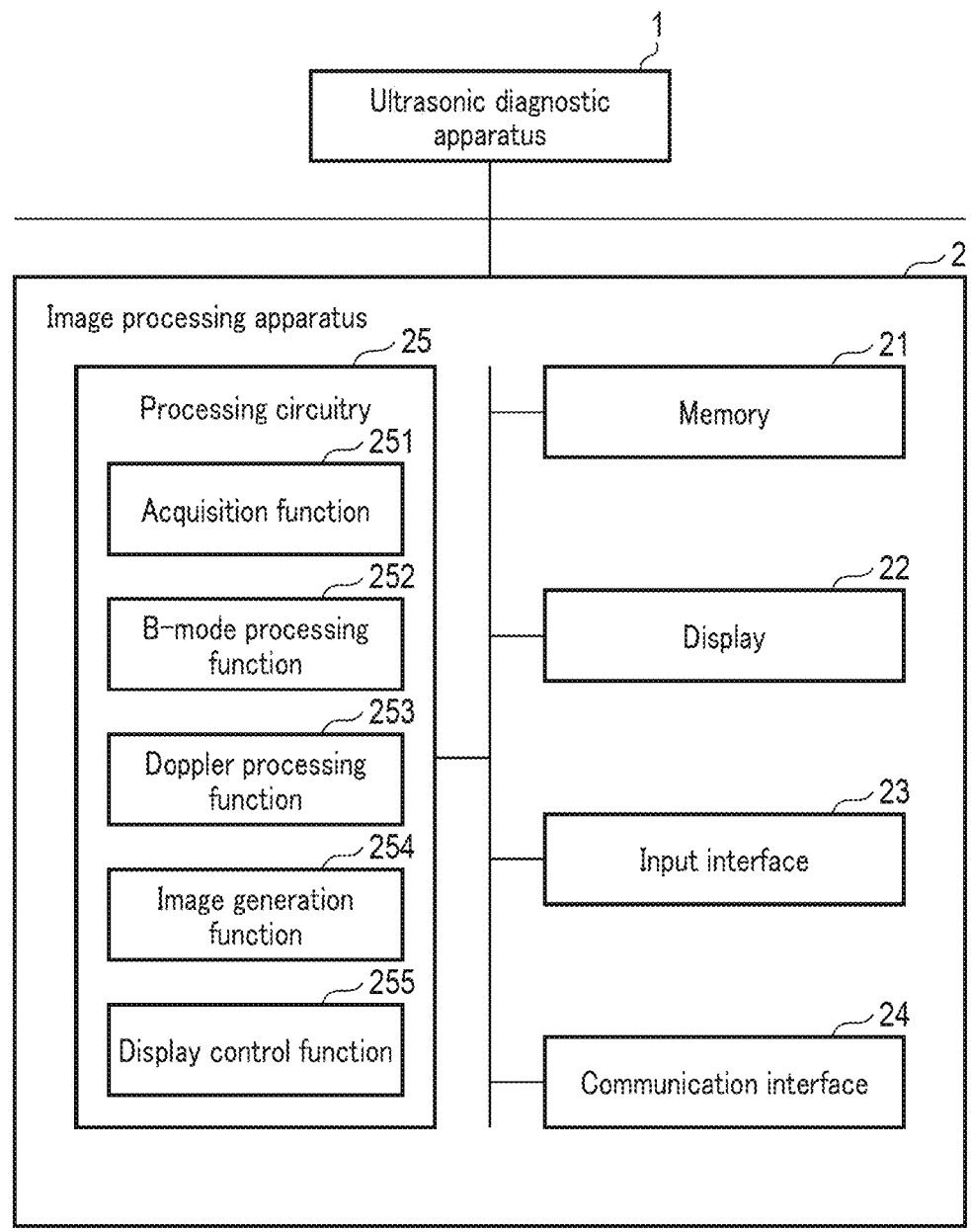
FIG. 7 is a block diagram showing a functional configuration of the image diagnostic apparatus according to another embodiment.

FIG. 7 is a block diagram showing an example of the functional configuration of the image processing apparatus 2 according to another embodiment. The image processing apparatus 2 shown in FIG. 7 includes a memory 21, a display 22, an input interface 23, a communication interface 24, and processing circuitry 25.

The processing circuitry 25 is a processor acting as a nerve center of the image processing apparatus 2, for example. The processing circuitry 25 executes a program stored in the memory 21 to realize a function corresponding to the program. The processing circuitry 25 has, for example, an acquisition function 251, a B-mode processing function 252, a Doppler processing function 253, an image generation function 254, and a display control function 255. In the present embodiment, the acquisition function 251, the B-mode processing function 252, the Doppler processing function 253, the image generation function 254, and the display control function 255 are realized by a single processor; however, the embodiment is not limited thereto. For example, processing circuitry may be constituted by combining a plurality of independent processors, and the respective processors may execute programs, thereby realizing the acquisition function 251, the B-mode processing function 252, the Doppler processing function 253, the image generation function 254, and the display control function 255. Dedicated hardware circuits capable of realizing the respective functions may also be incorporated.

The acquisition function 251 is a function of acquiring a reception signal from the ultrasonic diagnostic apparatus 1. The acquisition function 251 is an example of the acquisition unit. Specifically, for example, the processing circuitry 25 that enables the acquisition function 251 follows the instruction input via the input interface 23, and acquires a reception signal generated in the ultrasonic diagnostic apparatus 1.

The B-mode processing function 252 is a function of generating B-mode data, based on the reception signals received from the ultrasonic diagnostic apparatus 1.

The Doppler processing function 253 is a function of generating Doppler data based on a Doppler effect of a moving object present in an imaging ROI set in a scanning area, through performing a frequency analysis on the reception signal received from the ultrasonic diagnosis apparatus 1. Frequency filtering processing 1821, autocorrelation processing 1822, calculation processing 1823, blank processing 1824, spatial smoothing processing 1825, and time-direction smoothing processing 1826 are performed by the Doppler processing function 253.

The image generation function 254 is a function of generating various types of ultrasonic image data, based on data generated by the B-mode processing function 252 and/or the Doppler processing function 253.

The display control function 255 is a function of causing the display 22 to display ultrasonic image data of various kinds generated by the image generation function 254.

In each of the foregoing embodiments, an example in which the persistence coefficient is set to a first value if a magnitude of velocity change increases as time elapses, and is set to a second value if the magnitude does not increase, is described. However, the setting of the persistence coefficient is not limited to this example. For example, assume that the second value is a default value that is preset at the time of starting an examination, and that the first value is a value changed from the default value. The first and second values may be preset based on a type of examination. For example, in the examination of a heart, first and second values used for a heart examination are set, and in the examination of a kidney, first and second values used for a kidney examination are set.

The first and second values may be preset based on anatomical information of a target of examination. Anatomical information of a target of examination may be a shape or a size of the target, for example.

The first value, which is a value changed from a default value, may be a fixed value or a variable value. If the first value is a variable value, the first value may be varied so as to attenuate the weighting effect as the blood vessel comes closer to the periphery, for example. In this case, the degree of approximation to the peripheral blood vessels is known through associating the location of the ultrasonic probe 20 with the anatomical information, for example. The location of the ultrasonic probe 20 is acquired through a use of a location sensor system provided using a magnetic sensor, etc. Furthermore, the first value may be varied in accordance with a magnitude of velocity change that increases as time elapses, namely an amount of increase in acceleration. For example, the first value is varied so as to attenuate the effect of weighting in accordance with an amount of increase in acceleration. The first value may be determined by a combination at least of coefficients set based on an average velocity, a variance, a power, and a magnitude of velocity change of a blood flow. For example, if the persistence coefficient determined by the acceleration is α1, and the persistence coefficient determined by the average velocity is α2, the first value may be set to α1*α2.

In each of the foregoing embodiments, an example in which the persistence coefficient is changed if a magnitude of velocity change increases as time elapses is described. However, the changing of the persistence coefficient is not limited to this example. For example, if the magnitude of velocity change increases as time elapses, and if the degree is maintained, the persistence coefficient may be changed. In each of the foregoing embodiments, an example in which the persistence coefficient is changed if a magnitude of velocity change increases as time elapses is described.

According to at least one of the foregoing embodiments, the ultrasonic diagnostic apparatus 1 and the image processing apparatus 2 can suppress influences caused by the smoothing processing in a time-axis direction performed to generate a blood flow image on sharpness and a sense of pulsation of the blood flow image.

The term "processor" used in the above descriptions of the embodiment means, for example, circuitry such as a CPU (Central Processing Unit), a GPU (Graphics Processing Unit), an ASIC (Application Specific Integrated Circuit), or a programmable logic device (for example, an SPLD (Simple Programmable Logic Device), a CPLD (Complex Programmable Logic Device), or an FPGA (Field Programmable Gate Array), etc. A processor implements functions by reading and executing a program stored in the memory circuitry. The program may be directly incorporated into the circuit of the processor instead of being stored in the storage circuit. In this case, the processor implements the function by reading and executing the program incorporated into the circuit. Each processor of the above embodiment is not limited to being configured as a single circuitry, but may include a plurality of units of independent circuitry, in order to implement the functions. Furthermore, a plurality of constituent elements shown in FIG. 1 may be integrated into one processor to realize the functions.

While certain embodiments have been described, these embodiments have been presented by way of example only, and are not intended to limit the scope of the inventions. Indeed, the embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
an ultrasonic probe; and
processing circuitry configured to
  acquire a position of the ultrasonic probe:
  receive a reflected wave signal of an ultrasonic wave via the ultrasonic probe;
  generate a reception signal based on the received reflected wave signal;
  calculate blood flow information based on the reception signal;
  detect a magnitude of blood flow velocity change based on the blood flow information calculated at a plurality of points in time; and
  set a smoothing coefficient to a first value when the magnitude of blood flow velocity change between adjacent points in time increases;
  perform smoothing processing on the blood flow information in a time direction at an intensity determined in accordance with the detected magnitude of blood flow velocity change using the smoothing coefficient,
  wherein the processing circuitry is further configured set the first value so as to decrease as the acquired position of the ultrasonic probe moves toward periphery of blood vessels.

2. The ultrasonic diagnostic apparatus of claim 1, wherein the processing circuitry is further configured to detect a blood flow acceleration as the magnitude of blood flow velocity change.

3. The ultrasonic diagnostic apparatus of claim 1, wherein the processing circuitry is further configured to detect the magnitude of blood flow velocity change based on the blood flow information calculated at three points in time, the three points in time being at identical intervals.

4. The ultrasonic diagnostic apparatus of claim 3, wherein the three points in time are consecutive frames.

5. The ultrasonic diagnostic apparatus of claim 1, wherein the processing circuitry is further configured to
  set the smoothing coefficient to the first value when the magnitude of blood flow velocity change between adjacent points in time increases,
  set the smoothing coefficient to a second value that applies a greater weight to a past point in time than the first value when the magnitude of blood flow velocity change between adjacent points in time does not increase, and
  perform the smoothing processing on the blood flow information in the time direction using the smoothing coefficient.

6. The ultrasonic diagnostic apparatus of claim 1, wherein the processing circuitry is further configured to
  change the smoothing coefficient from a default value to the first value, which applies a greater weight to a current point in time than the default value when the magnitude of blood flow velocity change between adjacent points in time increases, not change the smoothing coefficient from the default value when the magnitude of blood flow velocity change does not increase, and perform the smoothing processing on the blood flow information in the time direction using the smoothing coefficient.

7. The ultrasonic diagnostic apparatus of claim 1, wherein the processing circuitry is further configured to set the smoothing coefficient to the first value when the magnitude of blood flow velocity change between adjacent points in time increases or is maintained, set the smoothing coefficient to a second value, which applies a greater weight to a past point in time than the first value when the magnitude of blood flow velocity change decreases, and perform the smoothing processing on the blood flow information in the time direction using the smoothing coefficient.

8. The ultrasonic diagnostic apparatus of claim 1, wherein the processing circuitry is further configured to change the smoothing coefficient from a default value to the first value, which applies a greater weight to a current point in time than the default value when the magnitude of blood flow velocity change between adjacent points in time increases or is maintained, not change the smoothing coefficient from the default value when the magnitude of blood flow velocity change decreases, and perform the smoothing processing on the blood flow information in the time direction using the smoothing coefficient.

9. The ultrasonic diagnostic apparatus of claim 6, wherein the default value and the first value are preset based on a type of examination.

10. The ultrasonic diagnostic apparatus of claim 6, wherein the default value and the first value are preset based on anatomical information of a target of examination.

11. The ultrasonic diagnostic apparatus of claim 7, wherein the first value and the second value are preset based on a type of examination.

12. The ultrasonic diagnostic apparatus of claim 7, wherein the first value and the second value are preset based on anatomical information of a target of examination.

13. The ultrasonic diagnostic apparatus of claim 6, wherein the first value, which is a value after being changed from the default value, is a fixed value or a variable value.

14. The ultrasonic diagnostic apparatus of claim 6, wherein the first value, which is a value after being changed from the default value, is determined by combining at least two of coefficients that are set based on an average velocity, a variance, a power, and a velocity change of a blood flow.

15. An image processing apparatus, comprising:
processing circuitry configured to
    acquire a position of an ultrasonic probe:
    acquire, via the ultrasound probe, a reception signal generated based on a reflected wave signal of an ultrasonic wave;
    calculate blood flow information based on the reception signal;
    detect a magnitude of blood flow velocity change based on blood flow information calculated at a plurality of points in time;
    set a smoothing coefficient to a first value when the magnitude of blood flow velocity change between adjacent points in time increases; and
    perform time-direction smoothing processing on the blood flow information at an intensity determined in accordance with the detected magnitude of blood flow velocity change using the smoothing coefficient,
wherein the processing circuitry is further configured to set the first value so as to decrease as the acquired position of the ultrasonic probe moves toward periphery of blood vessels.

* * * * *